United States Patent [19]
Dumas et al.

[11] Patent Number: 5,531,680
[45] Date of Patent: Jul. 2, 1996

[54] ENTERAL FEEDING PUMP MOTOR UNIT AND METHOD OF USE

[75] Inventors: Chris Dumas, Midvale; Sean Winterer, Sandy, both of Utah

[73] Assignee: Zevex, Inc., Salt Lake City, Utah

[21] Appl. No.: 435,735

[22] Filed: May 5, 1995

[51] Int. Cl.$^6$ ............................................. A61M 31/00
[52] U.S. Cl. .......................... 604/67; 604/151; 417/474
[58] Field of Search ........................ 604/65, 67, 151, 604/152, 153, 154, 155; 417/474, 476, 477.3; 415/900

[56] References Cited

U.S. PATENT DOCUMENTS

| | | | |
|---|---|---|---|
| 4,498,843 | 2/1985 | Schneider et al. | 604/65 X |
| 4,529,401 | 7/1985 | Leslie et al. | 604/67 X |
| 4,601,700 | 7/1986 | Thompson et al. | 604/65 |
| 4,884,013 | 11/1989 | Jackson et al. | |
| 4,919,650 | 4/1990 | Feingold et al. | 604/67 |
| 5,279,556 | 1/1994 | Goi et al. | 604/67 |
| 5,370,612 | 12/1994 | Maeda et al. | 604/65 X |

*Primary Examiner*—Corrine M. McDermott
*Assistant Examiner*—N. Kent Gring
*Attorney, Agent, or Firm*—Thorpe North and Western

[57] ABSTRACT

An Enteral Feeding Pump Motor Unit and Method of Use are disclosed. The motor unit uses optical sensors to monitor the rotational period and position of a platen of the motor unit. If the rotational period is different from a predetermined desired period, a controller in communication with the optical sensors and the platen changes the rate at which the platen rotates so as to effectuate movement of a desired amount of fluid through a delivery set passing through the motor unit. In accordance with one aspect of the invention, the optical sensors are disposed in an asymmetrical pattern to enable self-testing and to avoid ambiguous readings.

22 Claims, 6 Drawing Sheets

5,531,680

ENTERAL FEEDING PUMP MOTOR UNIT AND METHOD OF USE

BACKGROUND OF THE INVENTION

The present invention relates to the delivery of medical fluids, and in particular to an enteral feeding pump motor unit for precisely controlling the amount of such fluids that are received by a patient.

The use of enteral feeding pumps, in conjunction with a disposable delivery set, for the administering of medical fluids is well known in the medical arts. The delivery set will typically include two long sections of PVC tubing, connected to a centralized, shorter section of silicone tubing. The silicone section of the delivery set is mounted in the motor unit of an enteral feeding pump so that the silicone tube securely contacts a plurality of rollers mounted on a platen. The platen is in turn connected to a motor which selectively rotates the platen. As the platen rotates, the rollers apply pressure to the silicone section of the delivery set and force a predetermined amount of medicinal or nutrient solution through the delivery set with each rotation of the platen.

In order to control the rates at which the enteral feeding solution is delivered to the patient, numerous different approaches have been used to control the rate at which the solution passes through the pump and the delivery set. For example, it is known to control the rate at which the pump operates and therefore the amount of solution delivered to a patient. This has been accomplished by the use of stepper motors and the use of variable tension on the silicone tube in conjunction with a constant speed motor.

To further ensure that a precise volume of enteral fluid is supplied to the patient, the rotation of the platen is compared to a desired rotation to ensure that the appropriate amount of fluid is being delivered. While numerous different methods have been advanced for achieving precise control of the platen's rotation, and thus the rate of delivery to the patient, there is still substantial room for improvement in the control of platens, and thus precision in controlling the rate at which nutrient and medicinal fluids are delivered to a patient.

SUMMARY OF THE INVENTION

It is an object of the present invention to provide an improved method for regulating the rate at which a fluid is delivered to a patient by an enteral feeding pump.

It is another object of the present invention to provide an enteral feeding pump which incorporates the improved method, and which is inexpensive and easy to use.

It is another object of the present invention to provide safety mechanisms so that the enteral feeding pump may be checked to ensure that control devices on the pump are operating properly.

The above and other objects of the invention are realized in specific illustrated embodiments of an improved enteral feeding pump including a motor for selectively rotating a platen attached thereto. A plurality of optical sensing mechanisms are disposed adjacent the platen. The optical sensing mechanisms monitor rotation of the platen so as to provide the pump with precise information as to the actual position and rotation rate of the platen. This information may then be used by the pump to compensate for any difference between the actual rotation rate and a desired rotation rate. If the actual rotation and the desired rotation are substantially different, the actual rotation of the platen may be varied to achieve the desired volumetric rate of fluid delivery to the patient.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Figure 1:
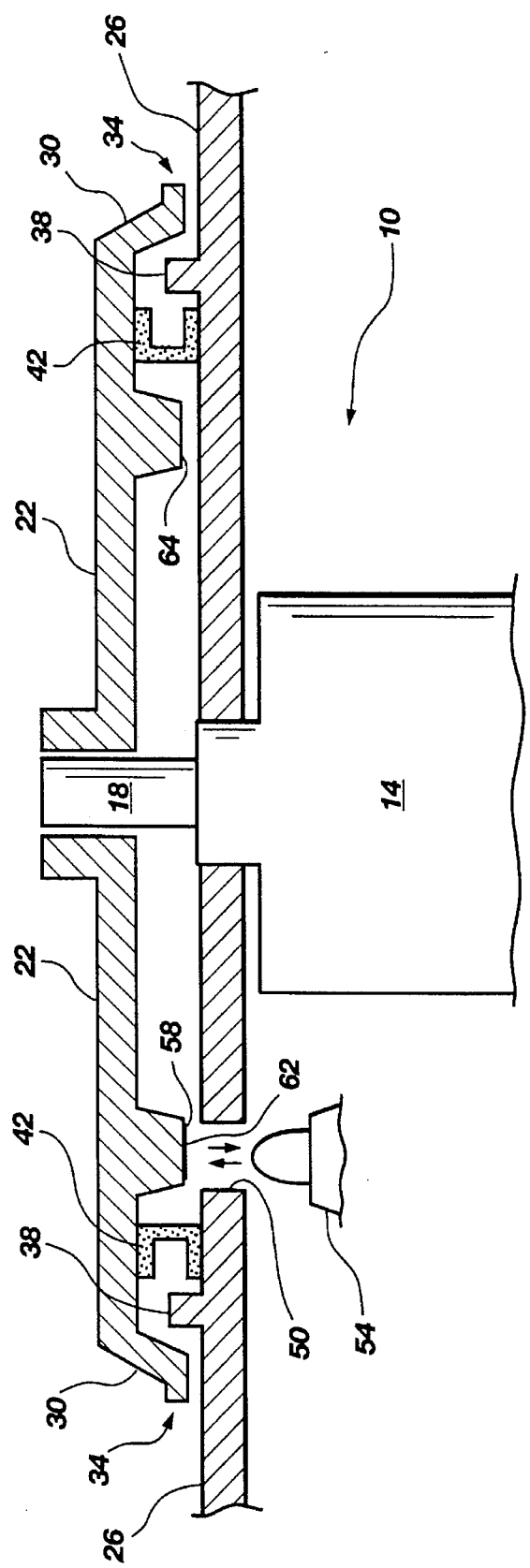
FIG. 1 is a fragmented cross-sectional view of a motor/platen unit of an enteral feeding pump for receiving a delivery set and made in accordance with the principles of the present invention.

Reference will now be made to the drawings in which the various elements of the present invention will be given numeral designations and in which the invention will be discussed so as to enable one skilled in the art to make and use the invention. Referring to FIG. 1, there is shown a fragmented side cross-sectional view of a motor unit, generally indicated at 10, of an enteral feeding pump. The motor unit includes a motor 14, which is connected by a shaft 18 to a platen 22. When the motor 14 is engaged, it rotates the shaft 18, thereby rotating the platen 22. A plurality of rollers (not shown) extend upwardly from the platen and force fluid through the delivery set.

The platen 22 extends outwardly and generally perpendicular to the shaft 18. Extending from the motor unit 14 below the platen 22, and generally parallel with the platen, is a motor casing 26. Along the outer edge the platen 22, a flange 30 extends downwardly toward the casing 26 so as to form a labyrinth seal 34 with a projection 38 extending upwardly from the casing 26. A flexible lip seal 42 is positioned inward of the labyrinth seal 34 to keep any foreign materials from working their way beneath the platen 22 and eventually below the motor casing 26.

At a mid point between the labyrinth seal 34 and the shaft 18, the casing 26 has a plurality of localized sensor slots 50 formed therein. A reflective sensor 54 is positioned below each slot and positioned to emit light through the slot and against an underside 58 of the platen 22, and provides an indication signal. As will be discussed with respect to FIG. 3, the underside 58 of the platen 22 is marked by a series of reflective surfaces 62 interspaced by nonreflective surfaces 64. When a reflective surface 62 is positioned above a localized sensor slot 50, the sensor 54 receives reflected light from the underside 58 of the platen 22 and emits an indication signal. When a nonreflective surface 64 is positioned above the localized sensor slot 50, the sensor 54 does not receive reflected light from the underside 58 of the platen 22 and does not emit an indication signal.

By counting the number of times the signal changes from reflective to nonreflective, and by monitoring the position of the reflective surfaces 62, the actual volume of nutrient or medicated fluid which is delivered to the patient can be determined, as well as the exact position of the platen 22. If these actual measurements differ within a given time period with the desired delivery rate and rotational rate of the platen 22, the period of the motor 14 can be adjusted to achieve the desired platen 22 rotation, and thus a desired fluid flow rate through the delivery set (not shown).

At most common flow rates, the pump motor 14 is actuated once per minute and the amount of angular rotation of the platen 22 during a period of one minute is compared to expected values in order to verify proper pump operation. At very low flow rates, the pump platen 22 turns a very small amount with each activation, requiring a period longer than one minute to measure angular rotation. Because the motor is activated periodically, at a predictable speed, over a fixed period of time, angular rotation can be measured optically to verify performance. Predictable variations in motor/platen speed caused by factors such as battery charge or connection to an alternating current power supply can be included in factors considered. If one of these factors influences the actual rate at which the platen 22 rotates, modifications can be made to activation timing to ensure that the desired flow rate is achieved.

Figure 2:
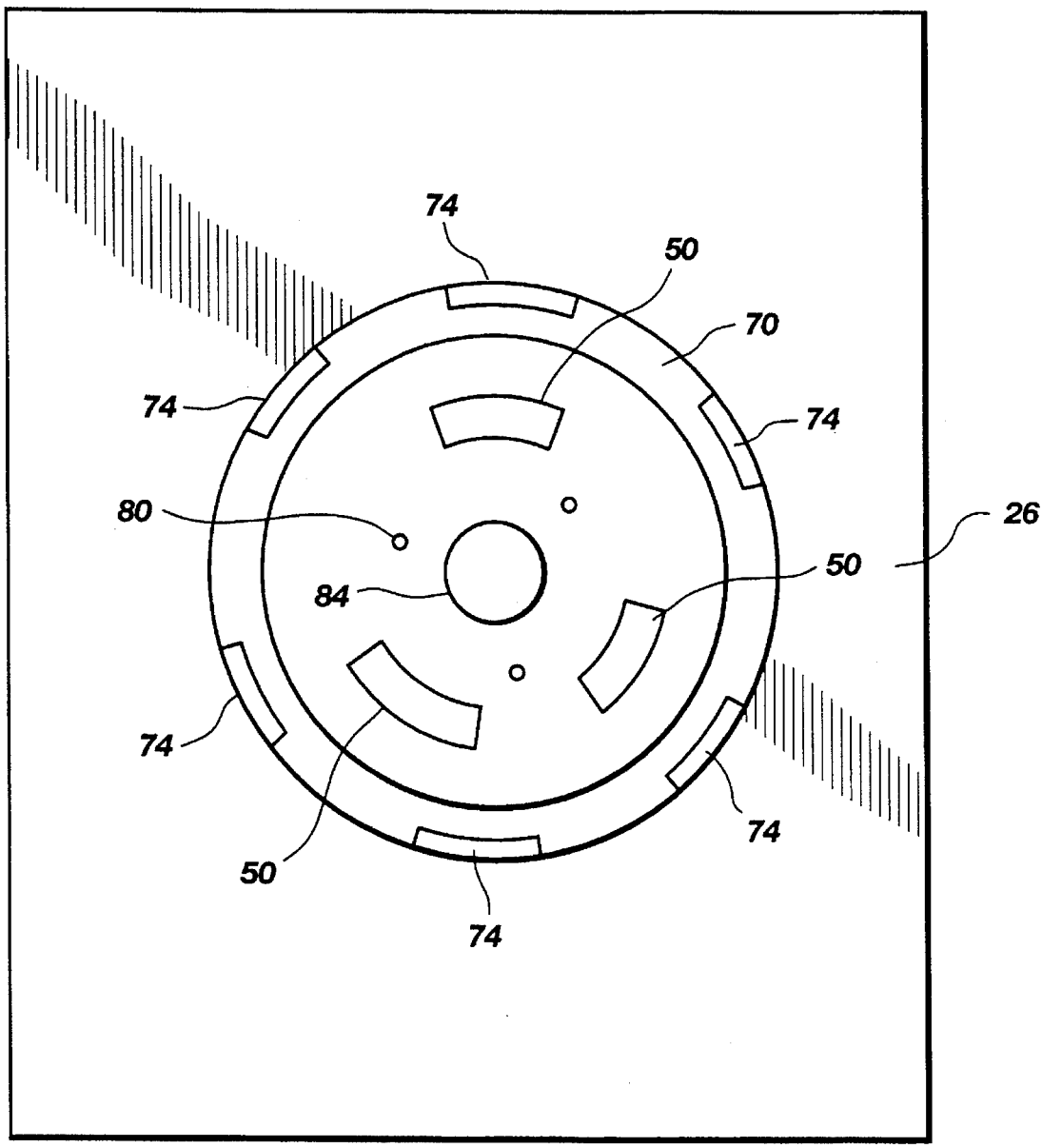
FIG. 2 is a plan view of the motor casing which is disposed below the platen in the enteral feeding pump of the present invention.

Referring now to FIG. 2, there is shown a plan view of the enclosure casing 26. An annular groove 70 is formed in the casing 26 for holding the lip seal 42 (FIG. 1). A plurality of retention tabs 74 are positioned around the annular groove 70 to hold the lip seal 42 in place during operation of the motor 14 (FIG. 1). The lip seal 42 nests in the annular groove 70 to prevent any foreign materials from working their way between the platen 22 (FIG. 1) and the casing 26 and disrupting the operations of the motor/platen unit 10 (FIG. 1).

Inside the annular groove 70 are the sensor slots 50 which are used by the reflective sensors 54 (FIG. 1) to monitor position of the platen 22 (FIG. 1). As is apparent from FIG. 2, the sensor slots 50 are positioned asymmetrically on the casing 26. The reason for such spacing will be discussed with respect to FIG. 3.

Inward of the sensing slots 50 are a plurality of mounting holes 80. A fastener (not shown) extends through each hole and into threaded holes in the motor housing so that the enclosure casing 26 and the motor 14 (FIG. 1) are held securely together. At a central point within the area defined by the annular groove 70 is a motor shaft hole 84. The motor shaft hole 84 allows the shaft 18 to extend from the motor 14 and support the platen 22 as is shown in FIG. 1.

Figure 3:
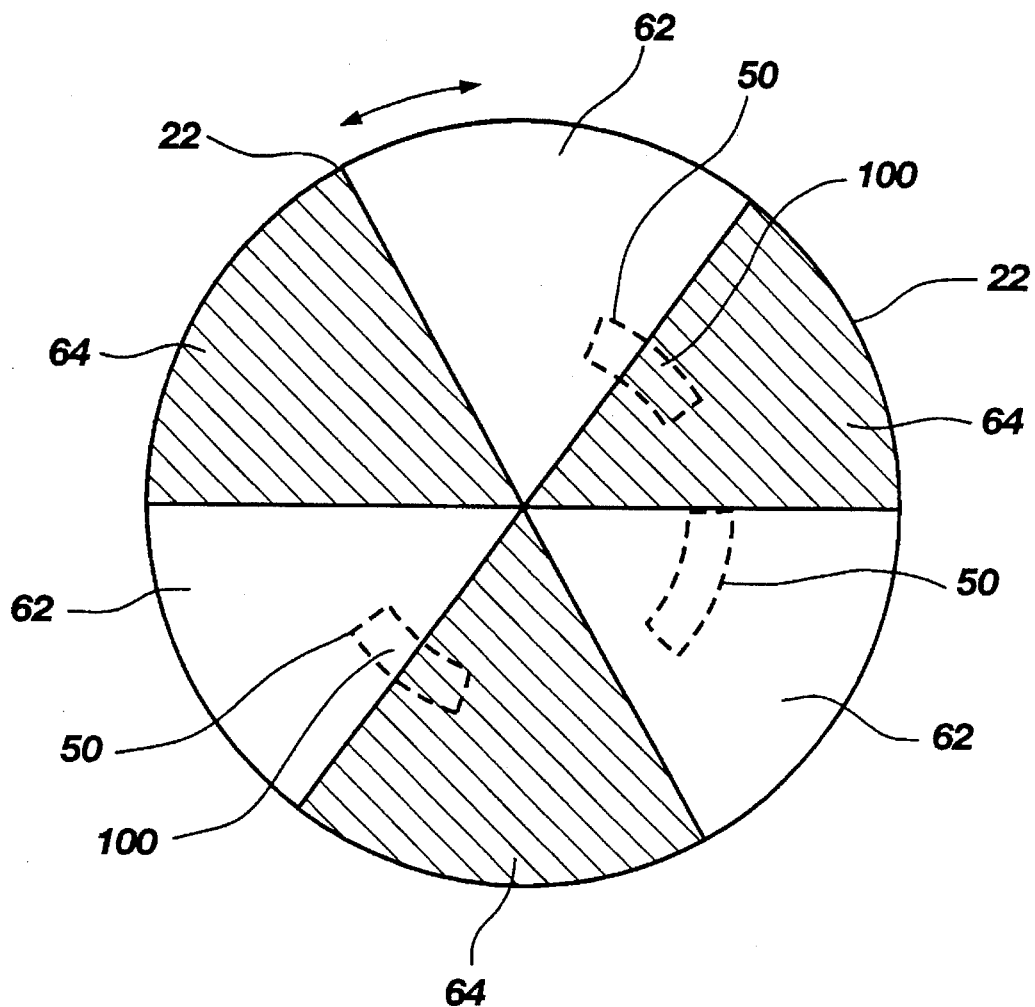
FIG. 3 is a schematic of the optical sensing mechanisms used in the present invention, disposed at select positions adjacent the platen.

Referring now to FIG. 3, there is shown a schematic representation of the underside of platen 22 (FIG. 1) and of the positioning of the sensor slots 50. As was mentioned previously, the sensor slots 50 are not evenly spaced. This is done to enable the sensors to self test and ensure that each sensor is working properly. This arrangement also prevents the pump from giving erroneous readings due to ambiguous signals which are received by the light sensors.

As shown in FIG. 3, the underside of the platen is divided into three light reflective surfaces 62 and three dark, nonreflective surfaces 64. While shown in the schematic as covering the entire section, the light, reflective surfaces 62 may be strips of a width about the same as that of the localized sensing slots 50 (FIG. 2) and disposed along a portion of the platen 22 which passes immediately above the sensor slots 50 as shown in FIG. 1.

As the platen 22 rotates, the reflective sensors 54 monitor changes in the position of the platen by sensing the light and dark surfaces, 62 and 64. When a border between a light surface 62 and a dark surface 64 falls adjacent a sensing slot 50, such as is shown at 100, the sensor will often emit an ambiguous signal. Thus, if a single sensor were used, it would be extremely difficult to determine whether or not the platen 22 is rotating. By positioning the localized sensor slots 50 asymmetrically, ambiguous signals are overcome by always having at least one sensor which provides a clear signal. The localized sensor slots 50 are positioned so that at any given time at least one sensor is well within a dark, nonreflective area, and at least one sensor is well within a light, reflective area. An ambiguous signal from the third sensor indicates that it is passing from a light, reflective area to a dark, nonreflective area, or vice versa, depending on which sensor is emitting the ambiguous signal.

Of additional concern is ensuring that the sensors are operative. If the circuitry in communication with the sensors 54 (FIG. 1) fails to indicate a signal received from a sensor, it indicates that the sensor is under a dark, nonreflective area. However, a similar response is received when the sensors 54 are not operating properly. To overcome this concern, the localized sensing slots 50, and thus the sensors 54, are disposed so that at least one slot and sensor is always positioned below a light, reflective surface of the platen 22. If the signals received from the sensors indicate that each sensor is positioned below dark, nonreflective areas, the motor unit must be discarded or repaired as such a signal indicates that the sensors are malfunctioning.

Those skilled in the art will appreciate the benefits which are derived from using at least three sensors. While using two sensors will work, the limitations involved due to difficulty in keeping one sensor adjacent a light, reflective surface, while avoiding ambiguous signals creates numerous problems. The use of three or more sensors overcomes these concerns and makes the readings received more reliable.

Figure 4:
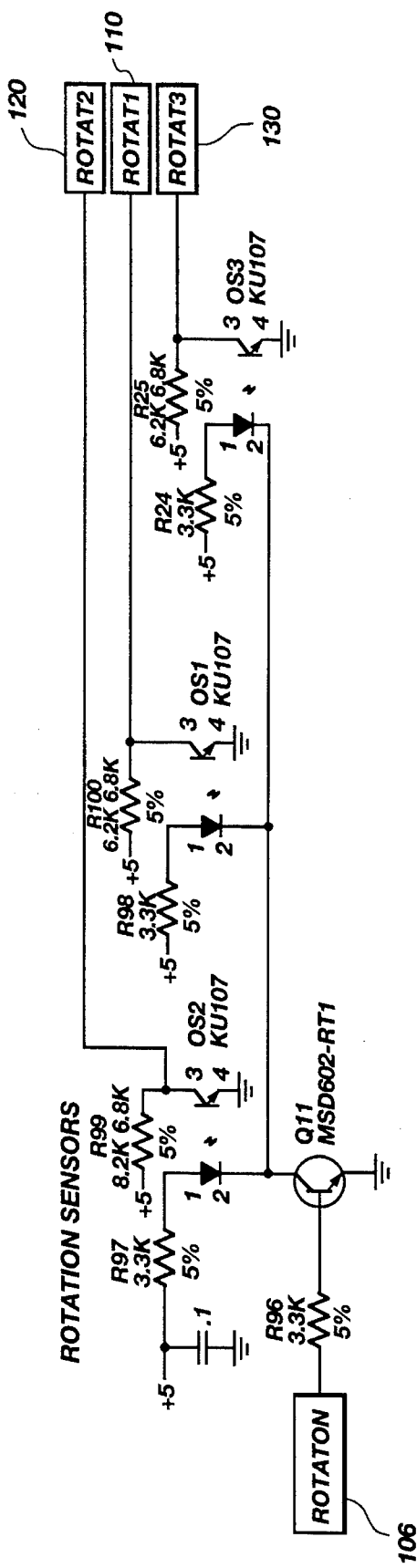
FIG. 4 is a schematic of the rotation sensors used in accordance with the principles of the present invention.

Referring now to FIG. 4, there is shown a schematic of the rotation sensors 54 used in the present invention. An input 106 provides a signal, and an output for each sensor, 110, 120 and 130, respectively, signals the existence of a light, reflective surface adjacent the sensor. Because of the asymmetrical placement of the sensors, at least one of the outputs 110, 120 and 130 will always provide a signal indicating the presence of the light, reflective surface adjacent the sensor. If all three provide no signal, the sensors will be replaced or the enteral feeding pump discarded, as the failure to produce at least one signal indicating a reflective surface confirms that the sensors are not working properly.

Figure 5:
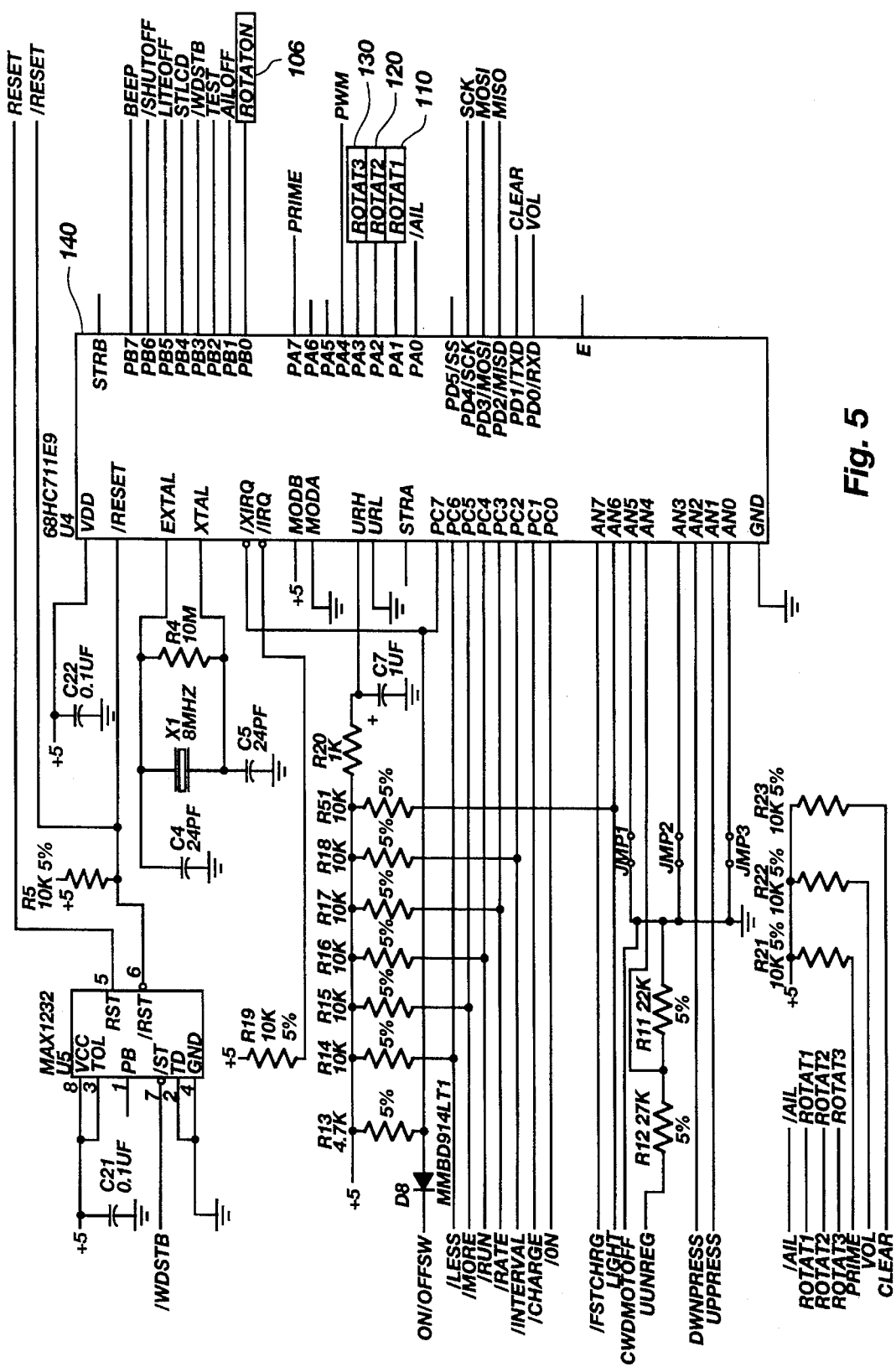
FIG. 5 is a schematic of a processing circuit as may be connected to the rotation sensors in accordance with the principles the present invention.

Referring now to FIG. 5, there is shown a schematic of a microprocessor and related circuitry which may be used with the present invention. The microprocessor 140 initiates the input 106 to the sensors as shown in FIG. 4. Responsive signals are fed to the microprocessor 140 via the first second and third outputs, 110, 120 and 130, respectively. In the event that the signals received from the outputs 110, 120 and 130, indicate that the platen 22 (FIGS. 1 and 3) is turning at a rate different than the rate necessary to achieve the desired rate of delivery, the microprocessor can increase or decrease the rotation period to achieve the desired fluid delivery.

Those skilled in the art will recognize numerous modifications which could be made to the present embodiment without departing from the spirit or scope of the invention. For example, the sensors shown could be replaced with other types of sensors which are currently available, or which become available in the future. Likewise, the microprocessor shown could be replaced by other microprocessors which will accomplish the same functions.

An additional modification which could be made would be to position the localized sensor slots 50 (FIGS. 2 and 3) in a symmetrical pattern. To achieve the advantages discussed above, the light, reflective surfaces, and the dark, nonreflective surfaces would be positioned asymmetrically about the bottom side 58 (FIG. 1) of the platen 22 (FIG. 1).

Figure 6:
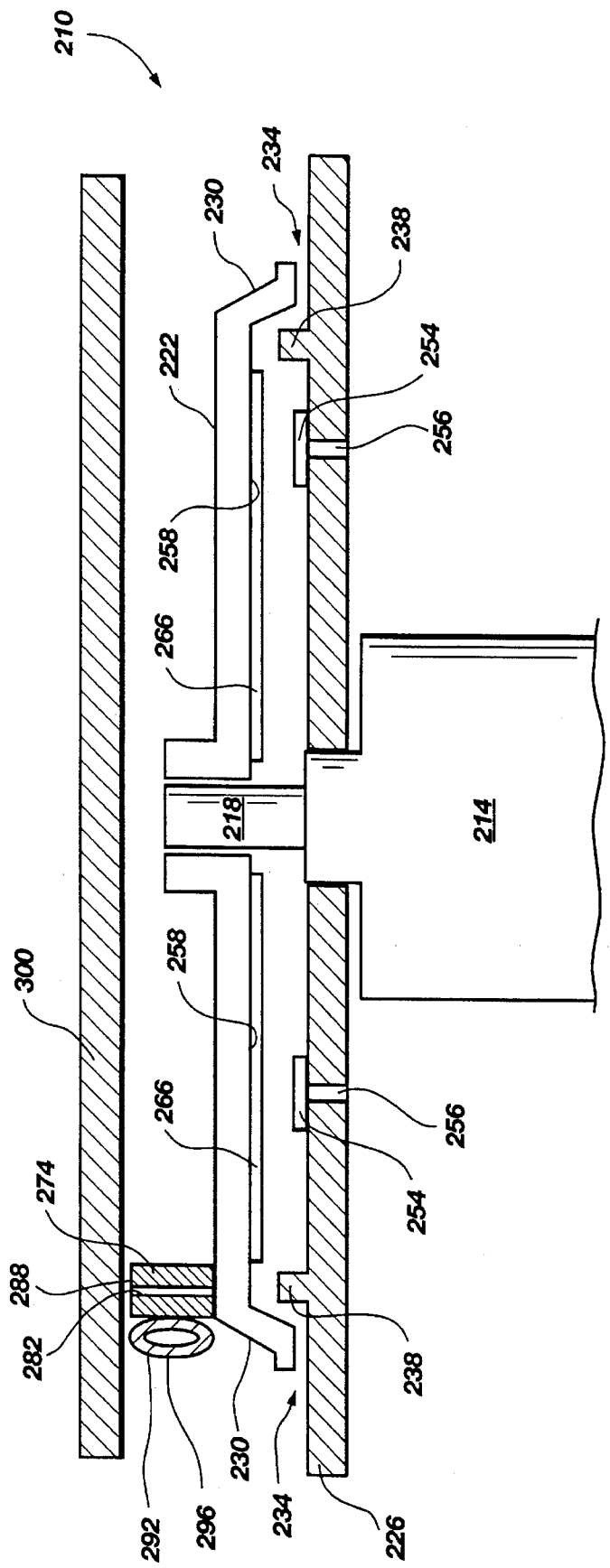
FIG. 6 is fragmented side cross-sectional view of an alternate embodiment of a motor/platen unit of an enteral feeding pump made in accordance with the principles of the present invention.

Referring now to FIG. 6, there is shown a fragmented side cross-sectional view of an alternate embodiment of the present invention. The motor/platen unit, generally indicated at 210, includes a motor 214 which is connected to a shaft 218. The shaft 218 extends through the middle of, and is connected to a rotatable platen 222 in any conventional manner (or manner developed hereafter).

A casing 226 extends from the motor 214 so as to be under and generally parallel with the platen 222. The platen 222 includes a flange 230 disposed adjacent a projection 238 from the casing 226 so as to form a labyrinth seal 234 similar to that discussed in FIG. 1. Inward of the projections 238, there are no localized sensor slots as were present in FIG. 1. Rather, the sensors 254 are mounted on the motor casing 226. A line 256 may extend through the casing 226 to enable communication of the sensors 254 with other circuitry, such as that shown in FIG. 5.

Also unlike the embodiment shown in FIG. 1, the underside 258 of the platen 222 is generally flat. Such a surface is advantageous in that it allows a partially reflective surface 266 to be applied to the underside 258 of the platen. Typically, the partially reflective surface 266 will have alternating light, reflective surfaces and dark, nonreflective surfaces as is shown in FIG. 2. The alternating light, reflective surfaces and dark, nonreflective surfaces will often be formed on a material, such as paper, with an adhesive backing. The partially reflective surface 266 can then be conveniently attached to the underside 258 of the platen 222 to simplify manufacture of the motor/platen unit 210.

Also shown in FIG. 6 is a roller 274 which extends upwardly from the platen 222 near the flange 230. The roller has a pin 282 extending through the center, and a rolling cylinder 288 disposed about the pin. As the platen 22 rotates, the roller 274 contacts a tube 292 of a delivery set. The tube 292 is usually made of silicone. As the roller 274 moves along the tube 292, sidewalls 296 of the tube are compressed together and any fluid in the tube is forced downstream. The rolling cylinder 288 rotates about the pin 282 so that excessive wear on the tube 292 will not occur as the platen 222 rotates. A cover plate 300 is also provided to help keep the tube 292 in place.

Each rotation of the platen 222 causes an small, known quantity of the fluid to be moved. Thus, by monitoring the rotations (and partial rotations) of the platen 222, the quantity of fluid which has been moved by the pump may be precisely determined. If the sensors 254 provide signals to the microprocessor 140 (FIG. 5) which indicate that the rotations of the platen 222 are different from that which is needed to achieve the desired flow rate, the microprocessor can adjust the period of the motor unit to ensure that the proper amount of fluid is being moved along the tube 292.

As with the other embodiment, numerous modifications could be made to the present embodiment without departing from the scope or spirit of the invention. Those skilled in the art will recognize numerous such modifications. For example, the sensors 254 could be mounted to the underside 258 of the platen 222. The partially reflective surface 266 would be mounted in an opposing fashion on the motor casing 226. Rotation of the platen 222 would cause relative movement between the sensors 254 and the partially reflective surface 266 which would function similarly to the embodiments described above.

Thus, there is disclosed an enteral feeding pump motor unit and method of use. The motor unit uses a plurality of optical sensors and alternating light reflective and nonreflective surfaces to determine the position of the platen and to test the sensors to ensure that they are working. If the actual rotation rate of the motor unit's platen differs from a predetermined desired rate, a controller adjusts motor period or rotation to ensure that the desired amount of nutrient or medicinal fluid is delivered to the patient. Numerous modifications of the present invention will be apparent to those skilled in the art, and the appended claims are intended to cover such modifications.

What is claimed is:

1. An enteral feeding pump motor unit for moving fluid through a tube of a delivery set at a desired rate, the motor unit comprising:

rotatable platen means disposed for receiving a tube of the delivery set and rotating to apply a moving mechanical force to at least one side of the tube and thereby move fluid through the tube when a tube is received by the platen means;

optical sensing means disposed adjacent the platen means for sensing rotation rate of the platen means, and for producing a signal indicative of the rate, at least a portion of the optical sensing means being disposed on the platen means; and control means responsive to the signal produced by the optical sensing means for signalling the platen means to modify the rotation period of the platen means to achieve fluid flow through the tube at the desired rate.

2. The enteral feeding pump motor unit of claim 1, wherein the motor unit further comprises a motor casing disposed adjacent and generally parallel with the platen means.

3. The enteral feeding pump motor unit of claim 1, wherein the optical sensing means comprises a plurality of light reflective surfaces disposed on an underside of the platen means.

4. The enteral feeding pump motor unit of claim 3, wherein the optical sensing means further comprises alternating light reflective surfaces and dark nonreflective surfaces.

5. The enteral feeding pump motor unit of claim 4, wherein the optical sensing means further comprises a plurality of sensors disposed adjacent the underside of the platen means.

6. The enteral feeding pump motor unit of claim 5, wherein the plurality of sensors are disposed such that at least one of the sensors is disposed below one of the light reflective surface at all times.

7. The enteral feeding pump motor unit of claim 4, wherein the alternating light reflective surfaces and dark nonreflective surfaces are arranged in an asymmetrical pattern.

8. The enteral feeding pump motor unit of claim 1, wherein the optical sensing means comprises a plurality of reflective sensors.

9. The enteral feeding pump motor unit of claim 1, wherein the optical sensing means comprises three sensors disposed adjacent the platen means in an asymmetrical pattern.

10. An enteral feeding pump motor unit for moving fluid through a tube of a delivery set at a desired rate, the motor unit comprising:

rotatable platen means disposed for receiving a tube of the delivery set and rotating to apply a moving mechanical force to at least one side of the tube and thereby move fluid through the tube when a tube is received by the platen means;

a motor casing disposed adjacent and generally parallel with the platen means;

optical sensing means disposed adjacent the platen means for sensing rotation rate of the platen means, and for producing a signal indicative of the rate; and control means responsive to the signal produced by the optical sensing means for signalling the platen means to modify the rotation period of the platen means to achieve fluid flow through the tube at the desired rate;

wherein the platen means comprises a downward sloping flange disposed about an outer perimeter of the platen means, and wherein the casing comprises an upwardly extending annular projection adjacent the flange of the platen means so as to form a labyrinth seal about the perimeter of the platen means.

11. An enteral feeding pump motor unit for moving fluid through a tube of a delivery set at a desired rate, the motor unit comprising:

rotatable platen means disposed for receiving a tube of the delivery set and rotating to apply a moving mechanical force to at least one side of the tube and thereby move fluid through the tube when a tube is received by the platen means;

a motor casing disposed adjacent and generally parallel with the platen means, a plurality of localized sensor slots being formed in the casing below the platen means;

optical sensing means disposed adjacent the platen means for sensing rotation rate of the platen means, and for producing a signal indicative of the rate; and control means responsive to the signal produced by the optical sensing means for signalling the platen means to modify the rotation period of the platen means to achieve fluid flow through the tube at the desired rate.

12. The enteral feeding pump motor unit of claim 11, wherein the plurality of localized sensor slots are disposed asymmetrically.

13. The enteral feeding pump motor unit of claim 11, where in the motor unit comprises at least three localized sensor slots.

14. The enteral feeding pump motor unit of claim 11, wherein the optical sensing means comprises at least one optical sensor disposed below each localized sensing slot.

15. An enteral feeding pump motor unit for moving fluid through a tube of a delivery set at a desired rate, the motor unit comprising:

rotatable platen means disposed to receive a tube of the delivery set and rotating to apply a moving mechanical force to at least one side of the tube and thereby move fluid through the tube, the platen means including a platen with an underside;

optical sensing means including alternating light reflective surfaces and nonreflective surfaces and a plurality of sensors disposed adjacent said surfaces, at least a portion of the sensing means being disposed on the platen, such that the sensors and surfaces are in an asymmetrical relationship to one another and such that the plurality of sensors sense the rotation rate of the platen means and produce a signal indicative of the rate; and control means responsive to the signal produced by the plurality of sensors for signalling the platen means to modify the rotation period of the platen means to achieve fluid flow through the tube at the desired rate.

16. The enteral feeding pump motor unit of claim 15, wherein the optical sensing means comprises at least three sensors disposed in an asymmetrical arrangement below the platen means.

17. The enteral feeding pump motor unit of claim 15, wherein the light reflective surfaces comprise material attached to the underside of the platen means.

18. A method for monitoring a rotation rate of a platen in an enteral feeding pump motor unit to ensure that a desired rotation rate is achieved, comprising:

a) providing a plurality of optical sensors;

b) positioning a plurality of reflective surfaces and nonreflective surfaces in an alternating pattern;

c) positioning one of the said optical sensors and said reflective and nonreflective surfaces adjacent the platen and the other of said optical sensors and said reflective and nonreflective surfaces on the platen such that rotation of the platen causes movement of the reflective and nonreflective surfaces relative to the optical sensors; and d) detecting the movement with light reflective surfaces with the optical sensors so as to determine an actual rotation rate of the platen.

19. The method according to claim 18, wherein a controller is provided in communication with the sensors and the platen, and wherein the method further comprises:

e) altering the period of rotation of the platen responsive to the actual rotation rate detected by the optical sensors when the actual rotation differs from the desired rotation.

20. The method according to claim 18, wherein step c) comprises, more specifically, affixing a plurality of light reflecting surfaces to the platen.

21. The method according to claim 20, wherein step c) further includes positioning the optical sensors in an asymmetrical pattern.

22. The method according to claim 20, wherein step c) further includes positioning the light reflective surfaces and the nonreflective surfaces in an asymmetrical pattern.

* * * * *